United States Patent
Austin

(10) Patent No.: US 7,992,273 B2
(45) Date of Patent: Aug. 9, 2011

(54) CRIMPING APPARATUS FOR REDUCING SIZE OF A STENT

(75) Inventor: Michael Austin, Co. Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 8 days.

(21) Appl. No.: 12/537,044

(22) Filed: Aug. 6, 2009

(65) Prior Publication Data

US 2010/0154195 A1 Jun. 24, 2010

Related U.S. Application Data

(60) Continuation of application No. 11/159,490, filed on Jun. 23, 2005, now Pat. No. 7,587,801, which is a continuation of application No. 10/444,807, filed on May 23, 2003, now Pat. No. 6,915,560, which is a division of application No. 09/966,686, filed on Oct. 1, 2001, now Pat. No. 6,823,576, which is a continuation of application No. 09/401,218, filed on Sep. 22, 1999, now Pat. No. 6,360,577.

(51) Int. Cl.
*B23P 19/04* (2006.01)
*B23P 11/00* (2006.01)
*B21D 41/00* (2006.01)

(52) U.S. Cl. .............. 29/283.5; 29/508; 29/516; 72/402

(58) Field of Classification Search .................... 29/508, 29/516, 283.5; 72/402

See application file for complete search history.

(56) References Cited

U.S. PATENT DOCUMENTS

| 1,665,915 | A | 4/1928 | Ekman |
| 1,889,795 | A | 12/1932 | Smith et al. |
| 2,292,421 | A | 8/1942 | Wolf |
| 2,751,077 | A | 6/1956 | Latin et al. |
| 2,887,222 | A | 5/1959 | Latin et al. |
| 2,986,192 | A | 5/1961 | Macleod |
| 3,084,389 | A | 4/1963 | Doyle |
| 3,664,213 | A | 5/1972 | Anati |
| 3,695,087 | A | 10/1972 | Tuberman |
| 3,731,518 | A | 5/1973 | Blocher |
| 3,736,788 | A * | 6/1973 | Olive-Jones et al. ........... 72/402 |

(Continued)

FOREIGN PATENT DOCUMENTS

DE 29506654.7 7/1995

(Continued)

OTHER PUBLICATIONS

Hawley's Condensed Chemical Dictionary, p. 873, 1993.

*Primary Examiner* — Jermie E Cozart
(74) *Attorney, Agent, or Firm* — Seager, Tufte & Wickhem LLC

(57) ABSTRACT

An apparatus for manipulating a medical device is formed of at least three coupled movable blades which are disposed about a reference circle to form an aperture whose size may be varied. The aperture capable of being sized to contain a medical device. Each blade is in communication with an actuation device which is capable of moving the blade to alter the size of the aperture. Each blade includes a single radial point which a) lies on the circumference of the reference circle prior to movement of the blade, and b) may be moved only along a radius of the reference circle on movement of the blade.

16 Claims, 15 Drawing Sheets

U.S. PATENT DOCUMENTS

| | | |
|---|---|---|
| 4,164,523 A | 8/1979 | Hanning |
| 4,350,036 A * | 9/1982 | Valente ............................ 72/402 |
| 4,404,827 A | 9/1983 | Van den Sype |
| 4,413,989 A | 11/1983 | Schjeldahl et al. |
| 4,434,645 A | 3/1984 | Svercl et al. |
| 4,454,657 A | 6/1984 | Yasumi |
| 4,456,000 A | 6/1984 | Schjeldahl et al. |
| 4,490,421 A | 12/1984 | Levy |
| 4,578,982 A | 4/1986 | Schrock |
| RE32,983 E | 7/1989 | Levy |
| 4,854,031 A | 8/1989 | Eisenzimmer |
| 4,906,244 A | 3/1990 | Pinchuk et al. |
| 4,942,756 A | 7/1990 | Charzewski |
| RE33,561 E | 3/1991 | Levy |
| 5,026,377 A | 6/1991 | Burton et al. |
| 5,087,394 A | 2/1992 | Keith |
| 5,108,415 A | 4/1992 | Pinchuk et al. |
| 5,156,612 A | 10/1992 | Pinchuk et al. |
| 5,163,989 A | 11/1992 | Campbell et al. |
| 5,183,085 A | 2/1993 | Timmermans |
| 5,195,350 A | 3/1993 | Aikens et al. |
| 5,261,263 A | 11/1993 | Whitesell |
| 5,270,086 A | 12/1993 | Hamlin |
| 5,275,777 A | 1/1994 | Chuang |
| 5,290,305 A | 3/1994 | Inoue |
| 5,304,340 A | 4/1994 | Downey |
| 5,334,146 A | 8/1994 | Ozasa |
| 5,338,172 A | 8/1994 | Williamson et al. |
| 5,358,486 A | 10/1994 | Saab |
| 5,381,686 A | 1/1995 | Thorup |
| 5,411,521 A | 5/1995 | Putnam et al. |
| 5,437,083 A | 8/1995 | Williams et al. |
| 5,509,184 A | 4/1996 | Herrero |
| 5,545,210 A | 8/1996 | Hess et al. |
| 5,546,646 A | 8/1996 | Williams et al. |
| 5,591,222 A | 1/1997 | Susawa et al. |
| 5,626,604 A | 5/1997 | Cottone, Jr. |
| 5,628,754 A | 5/1997 | Shevlin et al. |
| 5,630,830 A | 5/1997 | Verbeek |
| 5,672,169 A | 9/1997 | Verbeek |
| 5,700,285 A | 12/1997 | Myers et al. |
| 5,715,723 A | 2/1998 | Owens |
| 5,725,519 A | 3/1998 | Penner et al. |
| 5,738,674 A | 4/1998 | Williams et al. |
| 5,746,644 A | 5/1998 | Cheetham |
| 5,746,764 A | 5/1998 | Green et al. |
| 5,749,921 A | 5/1998 | Lenker et al. |
| 5,766,057 A | 6/1998 | Maack |
| 5,766,203 A | 6/1998 | Imran et al. |
| 5,792,415 A | 8/1998 | Hijlkema |
| 5,807,520 A | 9/1998 | Wang et al. |
| 5,810,871 A | 9/1998 | Tuckey et al. |
| 5,810,873 A | 9/1998 | Morales |
| 5,836,952 A | 11/1998 | Davis et al. |
| 5,836,965 A | 11/1998 | Jendersee et al. |
| 5,860,966 A | 1/1999 | Tower |
| 5,893,852 A | 4/1999 | Morales |
| 5,893,867 A | 4/1999 | Bagaoisan et al. |
| 5,911,752 A | 6/1999 | Dustrude et al. |
| 5,918,511 A | 7/1999 | Sabbaghian et al. |
| 5,920,975 A | 7/1999 | Morales |
| 5,931,851 A | 8/1999 | Morales |
| 5,935,476 A | 8/1999 | Langstedt |
| 5,951,540 A | 9/1999 | Verbeek |
| 5,974,652 A | 11/1999 | Kimes et al. |
| 5,992,000 A | 11/1999 | Humphrey et al. |
| 6,018,857 A | 2/2000 | Duffy et al. |
| 6,024,737 A | 2/2000 | Morales |
| 6,033,380 A | 3/2000 | Butaric et al. |
| 6,051,002 A | 4/2000 | Morales |
| 6,063,092 A | 5/2000 | Shin |
| 6,063,102 A | 5/2000 | Morales |
| 6,074,381 A | 6/2000 | Dinh et al. |
| 6,092,273 A | 7/2000 | Villareal |
| 6,108,886 A | 8/2000 | Kimes et al. |
| 6,125,523 A | 10/2000 | Brown et al. |
| 6,141,855 A | 11/2000 | Morales |
| 6,167,605 B1 | 1/2001 | Morales |
| 6,240,615 B1 | 6/2001 | Kimes et al. |
| 6,296,655 B1 | 10/2001 | Gaudoin et al. |
| 6,303,071 B1 | 10/2001 | Sugawara et al. |
| 6,309,383 B1 | 10/2001 | Campbell et al. |
| 6,360,577 B2 | 3/2002 | Austin |
| 6,364,870 B1 | 4/2002 | Pinchasik |
| 7,143,625 B2 | 12/2006 | Edin |
| 7,152,452 B2 | 12/2006 | Kokish |

FOREIGN PATENT DOCUMENTS

| | | |
|---|---|---|
| DE | 19532288 | 3/1997 |
| EP | 0630623 A2 | 12/1994 |
| EP | 0701800 A1 | 3/1996 |
| WO | 9000098 | 1/1990 |
| WO | 9603092 | 2/1996 |
| WO | 9720593 | 6/1997 |
| WO | 9819633 | 5/1998 |

* cited by examiner

CRIMPING APPARATUS FOR REDUCING SIZE OF A STENT

CROSS REFERENCE TO RELATED APPLICATIONS

This application is a continuation of U.S. patent application Ser. No. 11/159,490, filed Jun. 23, 2005, and entitled "METHOD AND APPARATUS FOR CONTRACTING, LOADING OR CRIMPING SELF-EXPANDING AND BALLOON EXPANDABLE STENT DEVICES," issued as U.S. Pat. No. 7,587,801, which is a continuation of U.S. patent application Ser. No. 10/444,807, filed on May 23, 2003, and entitled "APPARATUS FOR CONTRACTING, LOADING OR CRIMPING SELF-EXPANDING AND BALLOON EXPANDABLE STENT DEVICES," issued as U.S. Pat. No. 6,915,560, which is a divisional of U.S. patent application Ser. No. 09/966,686, filed on Oct. 1, 2001, entitled "METHOD AND APPARATUS FOR CONTRACTING, LOADING OR CRIMPING SELF-EXPANDING AND BALLOON EXPANDABLE STENT DEVICES," issued as U.S. Pat. No. 6,823,576, which is a continuation of U.S. patent application Ser. No. 09/401,218, filed on Sep. 22, 1999, entitled "APPARATUS FOR CONTRACTING, OR CRIMPING STENTS," issued as U.S. Pat. No. 6,360,577, which are all herein incorporated by reference.

BACKGROUND OF THE INVENTION

This invention relates to an apparatus and a method for reducing in size a medical device such as a stent, stent-graft, graft, or vena cava filter. The apparatus may be used in particular for fastening a medical device onto a catheter.

Medical devices such as stents, stent-grafts, grafts, or vena cava filters and catheters for their delivery are utilized in a number of medical procedures and situations, and as such their structure and function are well known.

A stent, for example, is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are typically inflation expandable or self-expanding. Self expanding stents which are constrained by a sheath or other restraining means, must be provided in a reduced diameter.

An example of a stent described in PCT Application No. 960 3092 A1, published 8 Feb. 1996.

In advancing a stent through a body vessel to the deployment site, the stent must be able to securely maintain its axial position on the delivery catheter, without translocating proximally or distally, and especially without becoming separated from the catheter. Stents that are not properly secured or retained to the catheter may slip and either be lost or be deployed in the wrong location. The stent must be crimped in such a way as to minimize or prevent altogether distortion of the stent and to thereby prevent abrasion and/or reduce trauma of the vessel walls.

In the past, this crimping or size reduction has been done by hand often resulting in the application of undesired uneven forces to the stent. Such a stent must either be discarded or re-crimped. Stents which have been crimped or otherwise reduced in size multiple times can suffer from fatigue and may be scored or otherwise marked which can cause thrombosis. A poorly crimped stent can also damage the underlying balloon.

Recently, stent crimping devices have been disclosed in U.S. Pat. No. 5,546,646 to Williams et al, U.S. Pat. No. 5,183,085 to Timmermans et al., U.S. Pat. No. 5,626,604 to Cottone, Jr., U.S. Pat. No. 5,725,519, U.S. Pat. No. 5,810,873 to Morales, WO 97/20593 and WO 98/19633.

A cam actuated stent crimper, shown in FIG. 1, employs a plurality of arc-shaped or curved slots with semi-circular ends, disposed such that each slot or cam engages a cam follower bearing 22. The arc-shaped or curved surfaces of the slots are inclined to be non-concentric relative to the axis of rotation 26, and therefore rotation of the cam plate 28 transmits equal radial displacements to the cam follower bearings 22, to simultaneously actuate a like number of linear bearings 24, which have their corresponding linear tracks or rails mounted on a fixed plate. As shown in FIG. 1 the cam plate rotary drive 29 comprises a pneumatic cylinder mounted on a pivot or trunnion, arranged with the cylinder rod connected rotatably to a short arm fixed rigidly to the cam plate. Accordingly, linear motion produced by the pneumatic cylinder translates into controllable arcs of motion of the circular cam plate, which has a projecting V-shaped profile on its outer edge in rolling engagement with three equally spaced rollers with mating inverse V-shaped profiles to provide precise rotatable support to the cam plate. Depending on the direction of rotation, the linear slides which each carry a radially disposed crimping blade, are either moved inwards to apply a crimping force to the stent, or outwards to release the stent. Also when crimping, depending on the degree of rotation of the cam plate, a specific radial crimping displacement may be obtained to match the diametral reduction required for any particular stent.

All US patents and applications and all other published documents mentioned anywhere in this application are incorporated herein by reference in their entirety.

BRIEF SUMMARY OF THE INVENTION

It would be desirable to produce a device capable of crimping a stent uniformly while minimizing the distortion of and scoring and marking of the stent due to the crimping. The present invention is directed to that end.

The present invention is particularly concerned with the crimping and otherwise reducing in size of inflation expandable stents, self-expanding stents and other expandable medical devices. For the purpose of this disclosure, it is understood that the term 'stent' includes stents, stent-grafts, grafts and vena cava filters. It is also understood that the term 'crimping' refers to a reduction in size or profile of a stent.

In the description that follows it is understood that the invention contemplates crimping a medical device either directly to a catheter tube or to a catheter balloon which is disposed about a catheter tube. When reference is made to crimping a medical device to a catheter, a balloon may be situated between the medical device and the catheter tube or the medical device may be crimped to a region of a catheter tube directly. The invention also contemplates crimping a stent in the absence of a catheter to reduce the stent in size.

The present invention is directed, in one embodiment, to an apparatus for reducing a medical device in size. Desirably, the medical device is a stent, a stent-graft, a graft or a vena cava filter, whether self-expandable, balloon expandable or otherwise expandable, although the inventive apparatus may also be employed with any other suitable, generally tubular medical device which must be reduced in size.

The inventive apparatus comprises at least three coupled movable blades disposed about a reference circle to form an aperture whose size may be varied. Each blade is in communication with an actuation device which is capable of moving the blade to alter the size of the aperture. Each blade includes a single radial point on the surface of the blade which a) lies on the circumference of the reference circle prior to movement of the blade, and b) may be moved only along a radius of the reference circle on movement of the blade.

The apparatus further includes an actuation device which comprises a cam and a plurality of linear slide devices. Each linear slide device is in communication with a blade. Each of the linear slide devices is also in mechanical communication with the cam. Rotation of the cam results in linear translation of the slide device and blade, such that the slide device moves along an axis parallel to the radius on which the radial point of the blade lies or along the radius itself.

The invention is also directed to an apparatus similar to that described above, with blades disposed about a reference tube to form a tubular aperture whose size may be varied. Each blade is in communication with an actuation device which is capable of moving the blade to alter the size of the tubular aperture. Each blade includes a single line which a) lies on the surface of the reference tube prior to movement of the blade, and b) may be moved only along a radial plane of the reference tube on movement of the blade.

The inventive apparatus finds particular utility in crimping a medical device such as those mentioned above to a catheter or to a balloon disposed about a catheter.

The inventive apparatus also finds utility in reducing the diameter of a medical device such as those mentioned above prior to crimping.

The invention is also directed to a method of manipulating a medical device which comprises the steps of providing the medical device and providing at least three blades capable of applying a radial inward force. The blades are disposed about a reference circle to form a shrinkable aperture. A medical device such as a stent is placed into the shrinkable aperture and the blades simultaneously moved inward to apply a radial inward force to the medical device. The blades are constructed and arranged such that each blade has a single point which a) lies on the circumference of the reference circle prior to movement of the blade, and b) is moved along a radius of the reference circle on movement of the blade.

The inventive apparatus may also be used as a variable size balloon mold. To that end, the invention is further directed to a method of molding a medical balloon. In the practice of the method, a balloon preform prepared through any suitable technique known in the art is provided. The preform is placed in an apparatus which has a shrinkable tubular aperture formed by at least three movable blades disposed about a reference tube. The blades are constructed and arranged such that each blade has a single line which a) lies on the surface of the reference tube prior to movement of the blade, and b) is moved along a radial plane of the reference tube on movement of the blade. The aperture may be set to a predetermined size prior to placement of the preform therein or after placement of the preform therein. An inflation fluid is supplied to the balloon preform to expand the balloon preform until it contacts the blades. The preform may optionally be heated prior to, during or after the blowing step. The thus formed balloon is then pressure relieved and removed from the apparatus.

BRIEF DESCRIPTION OF THE SEVERAL VIEWS OF THE DRAWING(S)

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
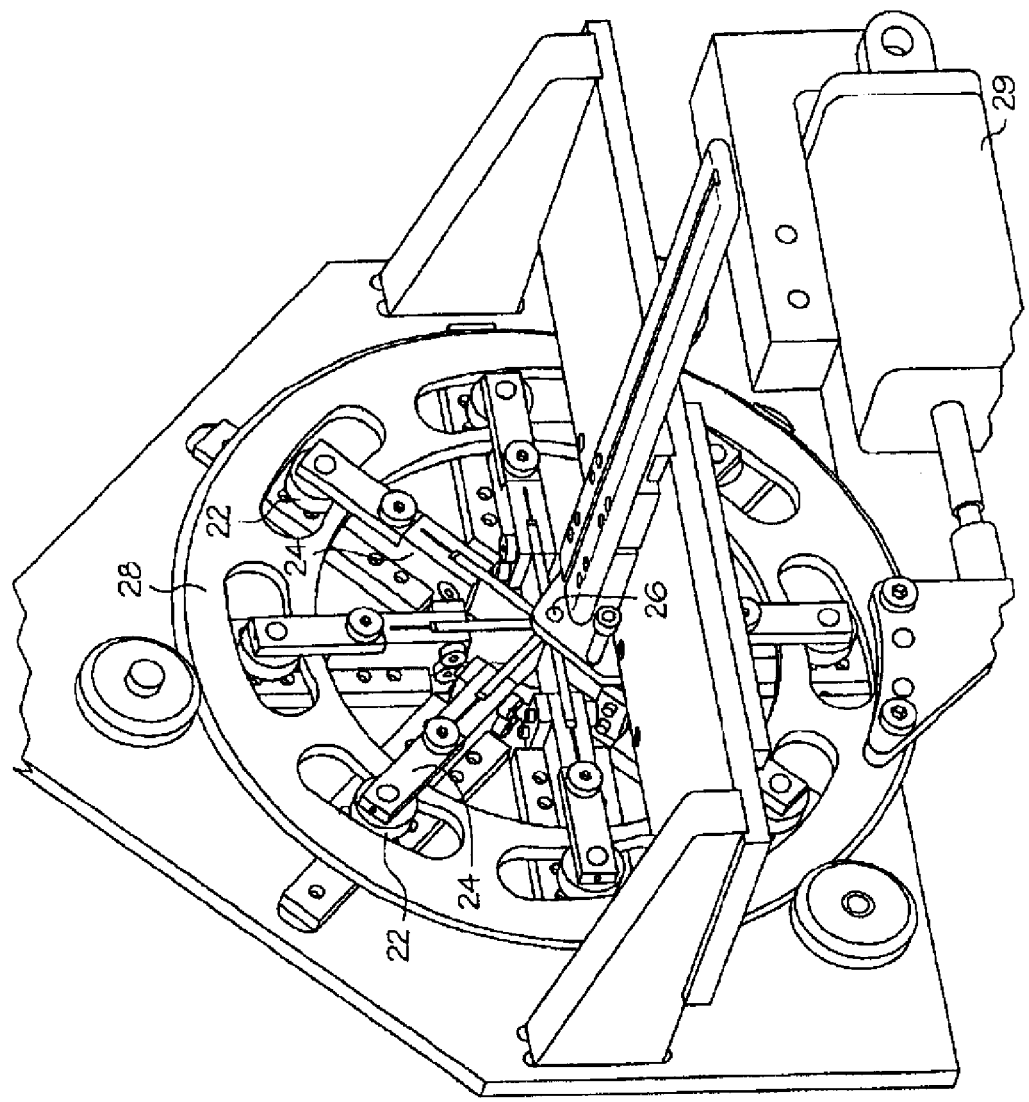
FIG. 1 shows a perspective view of a stent crimper.
Figure 2A:
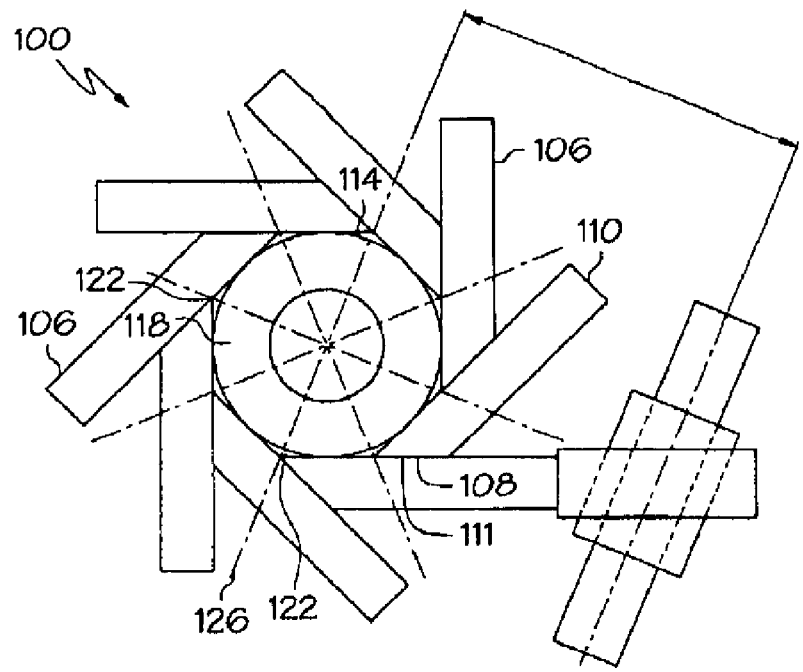
FIG. 2a is a schematic front view of an embodiment of the inventive apparatus.
Figure 2B:
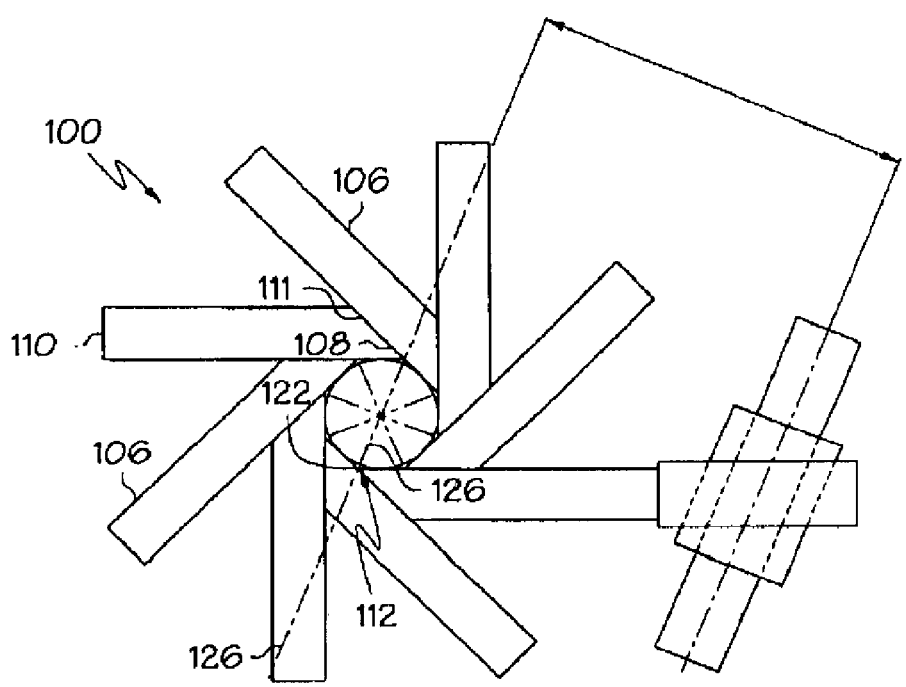
FIG. 2b is a schematic front view of the embodiment of FIG. 2a after the stent has been reduced in size.

As shown generally at 100 in FIGS. 2a and 2b, the inventive apparatus comprises eight coupled blades 106 disposed about a reference circle 114 to form an aperture 118 whose size may be varied. The apparatus may comprise as few as three blades and as many as sixteen or more blades. Desirably, the apparatus will have four or more blades and more desirably, eight or more blades. The maximum number of blades is limited only by how many blades can physically be coupled together under the relevant size constraints. As the number of blades is increased, the profile of the aperture and hence of the medical device following reduction in size, becomes smoother. FIG. 2b shows the apparatus of FIG. 2a after the stent has been reduced in size.

Figure 3A:
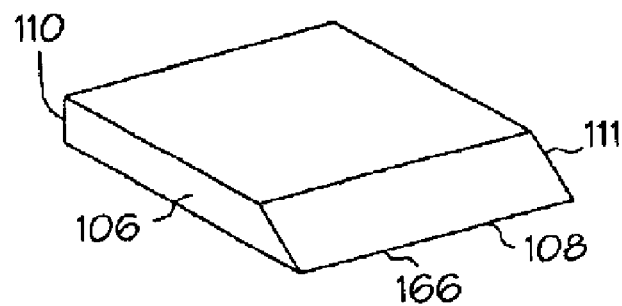
FIGS. 3a and 3b are schematics of blades.
Figure 3B:
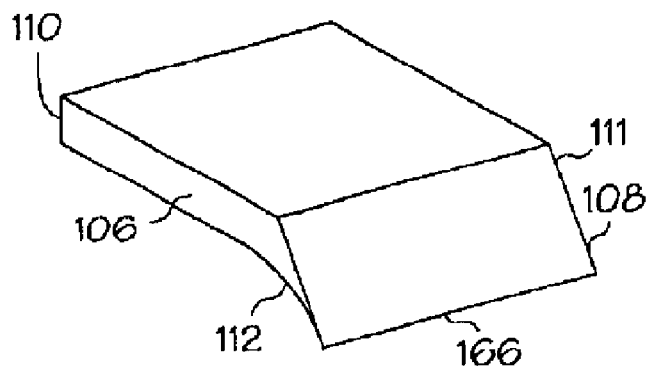
Figure 3C:
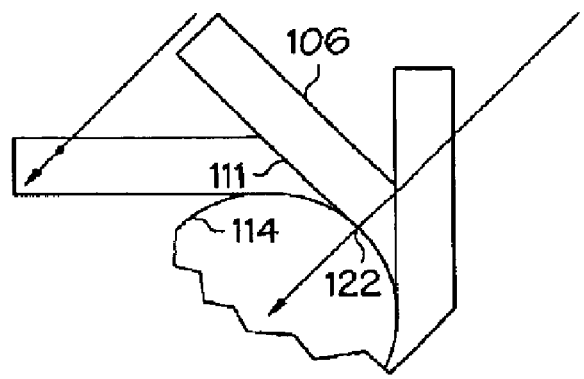
FIG. 3c is a partial schematic front view of an embodiment of the inventive apparatus employing the curved blades of FIG. 3b.

Blades 106 as shown in FIG. 3*a* have an inner end 108 which is desirably beveled 111 so as to mesh with adjacent blades and an outer end 110 which is displaced from aperture 118. Aperture 118 is polygonal. Blades 106 may also be shaped with a curved end 112, as shown in FIGS. 3*b* and 3*c* so as to form a substantially circular shaped aperture, when the aperture is fully closed.

Each blade 106 includes a single radial point 122 which lies on a radial line 126 of reference circle 114 prior to movement of blade 106 and which may be moved only along the radius 126 of reference circle 114 on movement of blade 106. Desirably, the single radial point 122 will be disposed at the tip of the blade adjacent to beveled end 111.

Figure 4A:
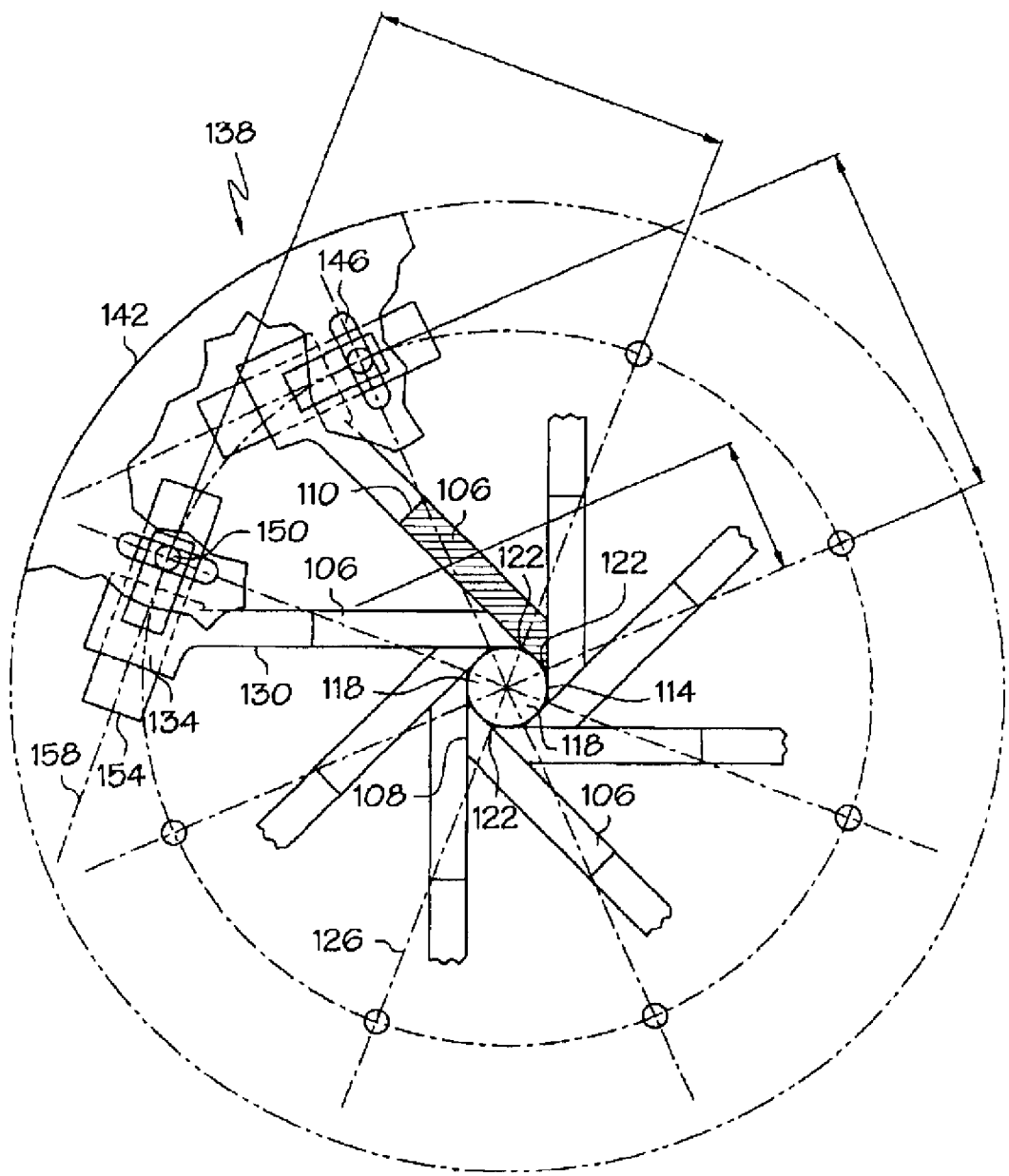
FIG. 4a is a partial front view of an embodiment of the inventive apparatus.

In the embodiment shown in FIG. 4*a*, radial point 122 lies at the tip of blade 106. Each blade 106 has a connecting link 130 extending from second end 110. Connecting link 130 ends in mounting means 134, typically a mounting flange adapted for attachment to a linear bearing block, for interfacing with an actuation device, shown generally at 138. Actuation device 138 is capable of simultaneously moving blades 106 to alter the size of aperture 118. Actuation device 138 includes actuation plate 142 which is coaxial with reference circle 114. Actuation plate 142 has eight equi-spaced radial slots 146. More generally, for every blade there will be a corresponding radial slot on actuation plate 142. Each radial slot 146 overlaps a mounting means 134 for a linear bearing block at the end of a connecting link 130. Each blade 106 is engaged to actuation plate 142 via a cam follower bearing 150 disposed in radial slot 146 and attached to mounting means in slotted end 134.

Each bearing 150 extends from a linear slide 154. Linear slide 154 is mounted on a non-rotating plate 156 (shown in FIG. 8). Linear slide 154 is constructed and arranged to slide along a line 158 which is parallel to the radius 126 on which radial point 122 of blade 106 lies.

Figure 4B:
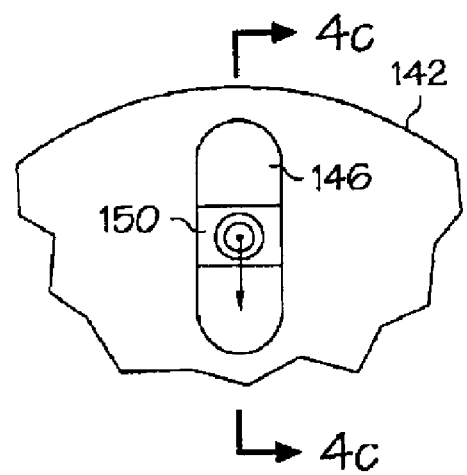
FIG. 4b is a partial front view of an embodiment of the inventive apparatus.
Figure 4C:
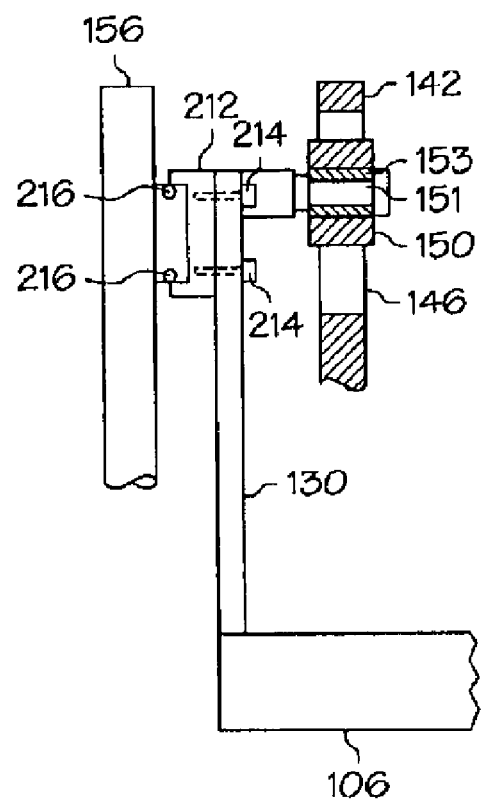
FIG. 4c shows a side view of the embodiment of FIG. 4b taken along lines 4c-4c.

For the purposes of this disclosure, the term 'cam follower bearing' includes cam follower bearings, low friction rollers, roller bearings, needle roller bearings and a slipper block pivot mounted on a bearing and stub shaft. FIG. 4*b* is a partial front view of an embodiment in which a slipper block is used. A side view of the embodiment of FIG. 4*b* taken along lines 4*c*-4*c* is shown in FIG. 4*c*. Slipper block 150 resides in slot 146 of actuation plate 142. Slipper block 150 is mounted on stub shaft 151 which extends from connecting link 130. Desirably, bearings 153 will be present between shaft 151 and slipper block 150. Connecting link 130, in turn, is fastened to linear bearing block 212 via fasteners 214. Bearing block 212 is linearly mounted on linear slide which is mounted on fixed plate 156. Linear motion is facilitated by the presence of bearings 216.

Cam follower bearing 150 may be replaced by any other suitable connecting member which can connect the slide and the link.

In use, as actuation plate 142 is rotated in a clockwise direction, the clockwise motion of the actuation plate is translated into linear motion of each of linear slide 154 and blade 106 via bearing 150. Each blade 106 moves outward in a direction parallel to the radius 126 on which the radial point 122 of the blade 106 lies, resulting in the opening of aperture 118. As actuation plate 142 is rotated in a counterclockwise direction, each blade 106 moves inward in a direction parallel to the radius 126 on which the radial point 122 of the blade 106 lies, resulting in the closing of aperture 118. As aperture 118 closes, a radially inward force is applied to a medical device disposed in the aperture. The actuation plate is rotated until the desired size reduction of the aperture and medical device has been achieved. Following the reduction, the actuation plate is rotated in the opposite direction to allow for removal of the medical device from the aperture.

The apparatus may be used to reduce the diameter of a suitable medical device such as those disclosed above or may be used to crimp a medical device to a catheter.

Figure 5A:
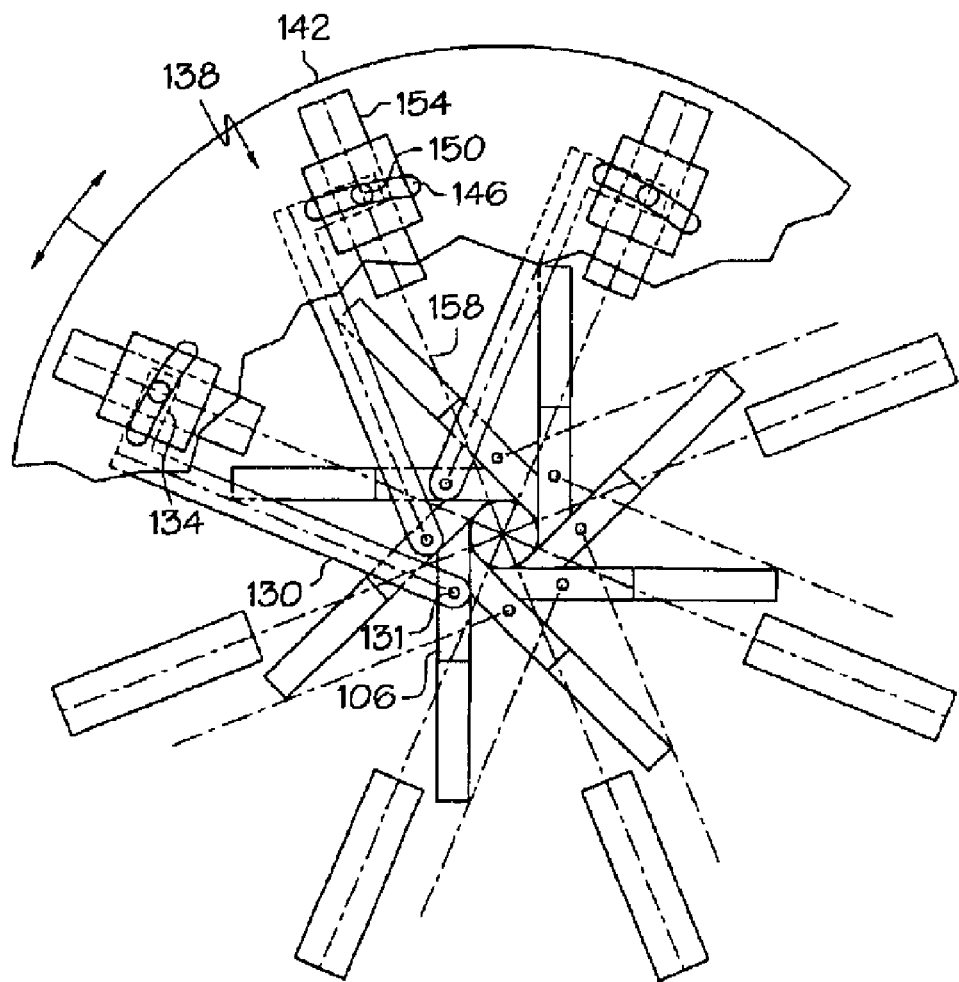
FIG. 5a shows a partial front view of another embodiment of the inventive apparatus.

Another embodiment of the invention is shown in FIG. 5*a*. Each blade 106, as shown in FIG. 5*a*, has a connecting link 130 extending therefrom. Connecting link 130 is rigidly attached to blade 106. Connecting link 130 ends in an angled end 134 for interfacing with an actuation device, shown generally at 138. Actuation device 138 is capable of simultaneously moving blades 106 to alter the size of aperture 118.

Actuation device 138 includes a rotatable actuation plate 142 which is co-axial with reference circle 114. Rotatable actuation plate includes cam slots 146 which are not concentric with the axis of rotation, arcing inward. Each connecting link 130 is engaged to actuation plate 146 via a cam follower bearing 150 disposed in slot 146 and attached to both angled end 134 of connecting link 130 and to a linear slide 154. Linear slide 154 is mounted on a non-rotating plate similar to that shown in FIG. 8. Linear slide 154 is constructed and arranged to slide along a radial line 158 on which radial point 122 of blade 106 lies.

Figure 5B:
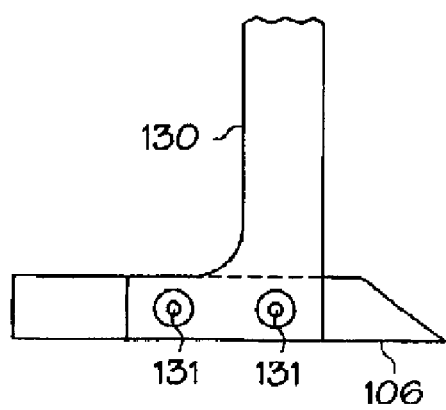
FIG. 5b shows a link connected to a blade.

Connecting link 130 may be bonded adhesively, welded, joined with a fastener or otherwise joined to blade 106. As shown in FIG. 5*a*, a single screw 131 is used to connect link 130 to blade 106. FIG. 5*b* shows a connecting link 130 including a right angle portion which is fastened to a blade 106 using two screws 131. Connecting link 130 and blade 106 may optionally be formed of a single piece of material. Regardless of how the connecting member is joined to the blade, no movement of the blade relative to the connecting link is permitted.

In use, as actuation plate 142 is rotated in a clockwise direction, the clockwise motion of the actuation plate is translated into a linear outward motion of each of linear slides 154 and blades 106 via bearings 150 resulting in the opening of aperture 118. The outward motion results from the radially outward arcing of cam slot 146. As actuation plate 142 is rotated in a counterclockwise direction, each blade 106, because of the radially inward arc of cam slots 146, moves inward in a direction parallel to the radius 126 on which the radial point 122 of the blade 106 lies, resulting in the closing of aperture 118. As discussed above, as the aperture is decreased in size, a radial inward force is brought to bear against a medical device disposed in the aperture, thereby reducing the size of the medical device.

The embodiment of FIG. 5*a* differs from the embodiment of FIG. 4*a* in that in the embodiment of FIG. 5*a*, the slide moves along the radial line on which the radial point of the attached blade lies whereas in FIG. 4*a* the slide moves parallel to the radial line. In both of the embodiments, each of the blades is constrained with two degrees of freedom to satisfy the condition that the movement of the tip be radial in accordance with the invention.

In the embodiments of FIGS. 4*a* and 5*a*, the slots in the actuation plate are constructed and arranged to allow for a sufficient reduction in size of the aperture so that a medical device can be reduced in size to a desired diameter. Those of ordinary skill in the art will recognize other suitable actuation devices that may be used in the practice of this invention.

Desirably, in the above embodiments, the blades will be as long as or longer than the medical device disposed within so that the medical device is uniformly reduced in size along its entire length.

Figure 6:
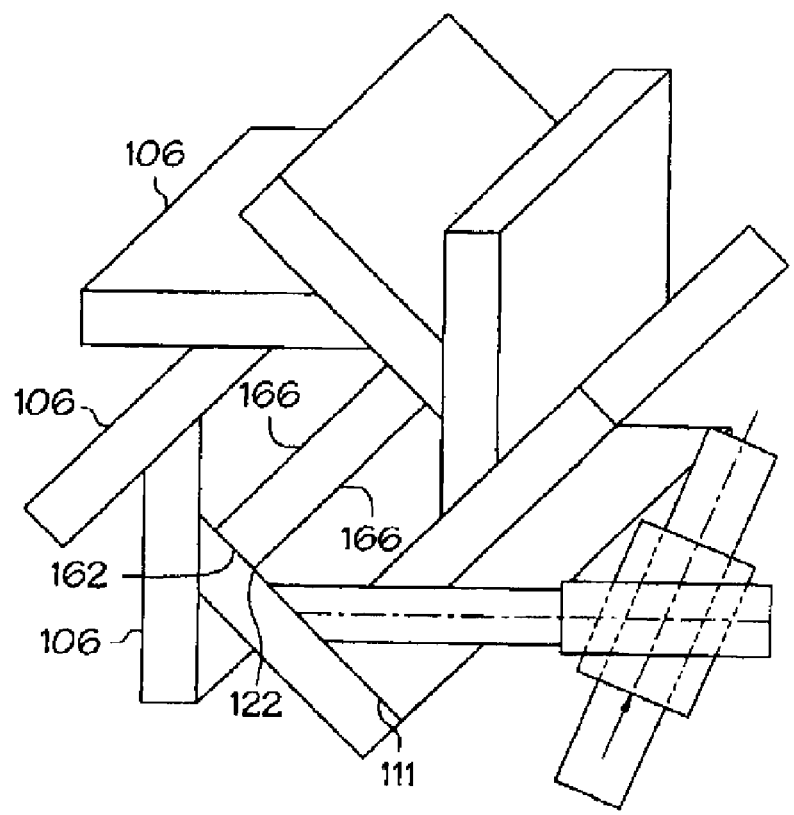
FIG. 6 is a schematic, perspective view of an embodiment of the inventive apparatus.
Figure 7:
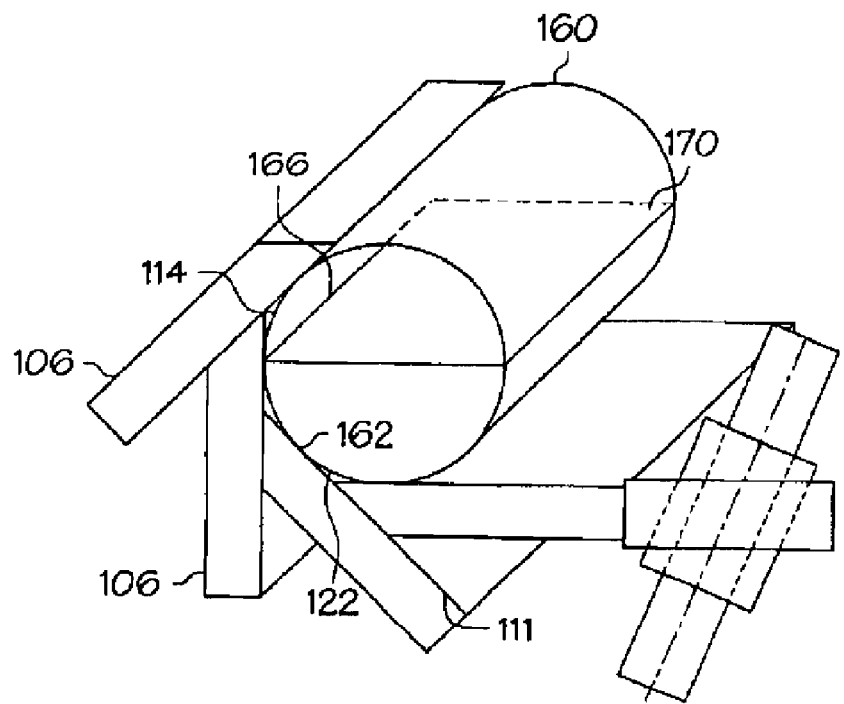
FIG. 7 shows a partial view of the embodiment of FIG. 6.

This is illustrated in the embodiment of FIGS. 6 and 7 and further in FIGS. 3*a* and 3*b* in which blades 106 are disposed about a reference tube 160 to form a tubular aperture 162 whose size may be varied. Reference circle 114 is seen to lie along reference tube 160. Each blade 106 is in communication with an actuation device such as that shown in FIG. 4 or 5. The actuation device is capable of moving blades 106 to alter the size of tubular aperture 162. Each blade 106 includes a single line 166 which a) lies on a radial plane 170 of the reference tube 160 prior to movement of blade 106, and b) may be moved only along a radial plane 170 of reference tube 160 on movement of blade 106. Desirably, reference tube 160 is cylindrical and exceeds the length of the medical device to be reduced in size.

Figure 8A:
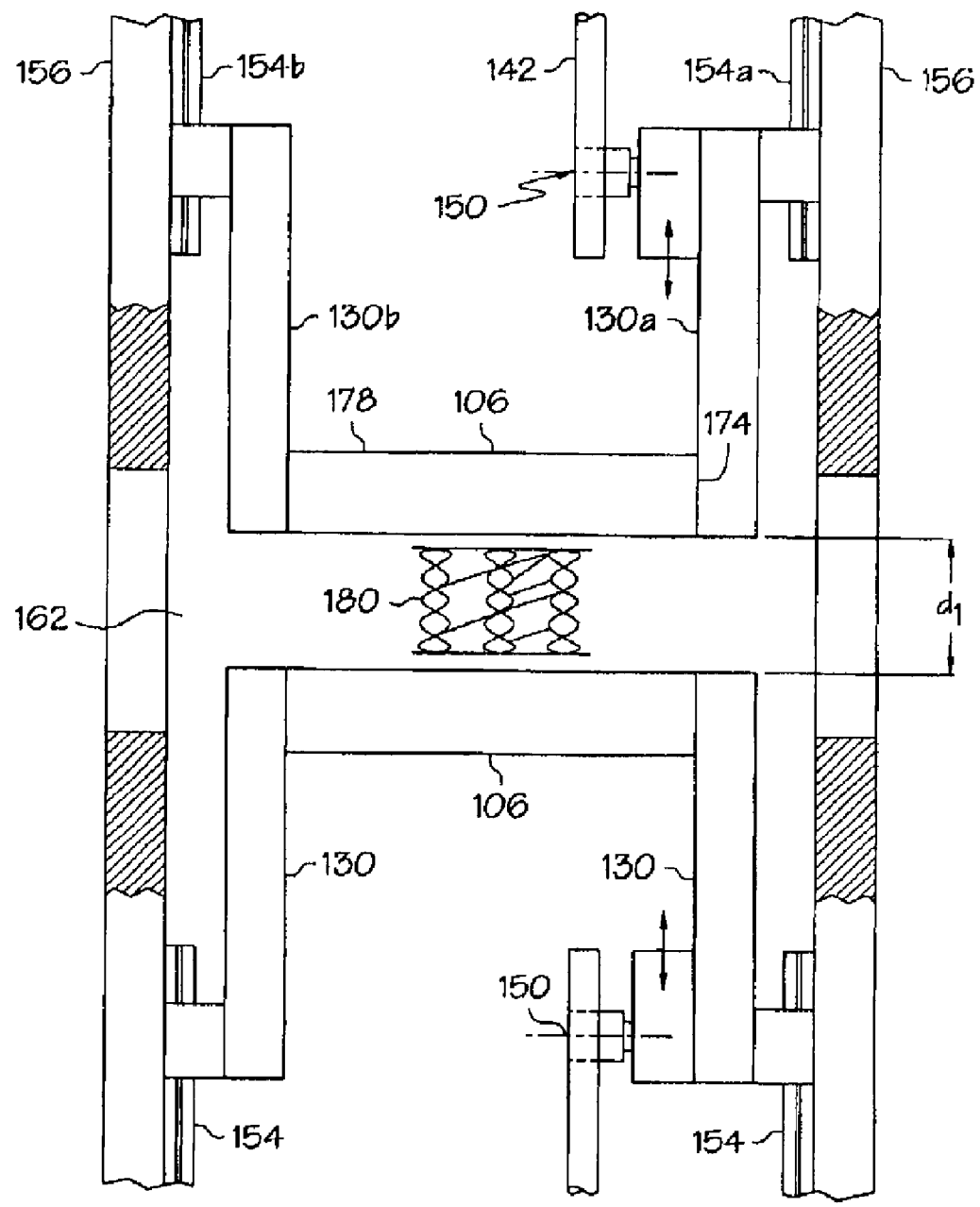
FIGS. 8a and 8b are partial side elevational views of an embodiment of the inventive apparatus taken along a radial plane during the size reduction process.
Figure 8B:
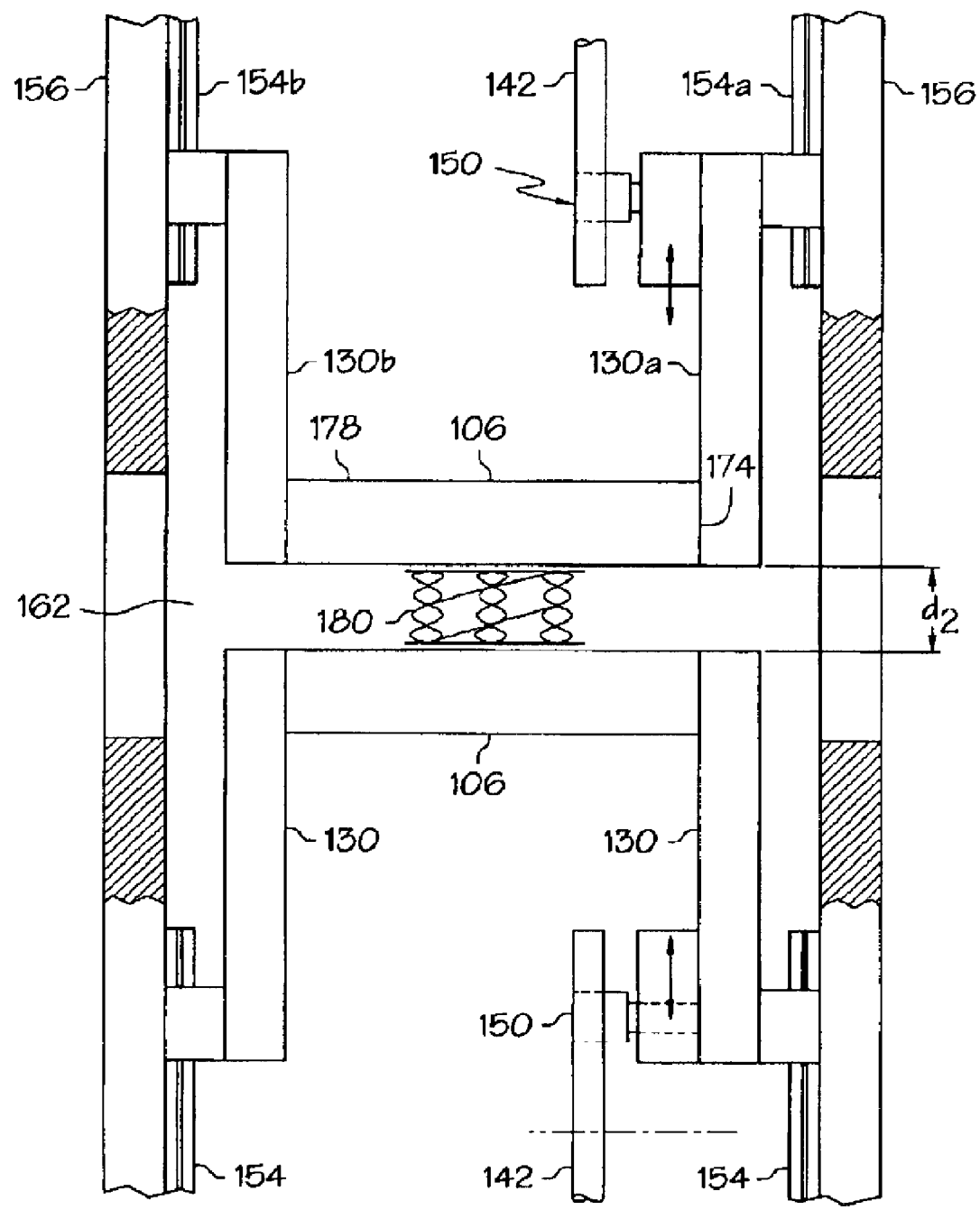

Another embodiment of the invention is illustrated in FIGS. 8a and 8b. In the embodiment of FIGS. 8a and 8b, two non-rotating plates 156 are present, one at each end of the apparatus. Each blade 106 is connected at first end 174 to a linear slide 154a via a connecting link 130a and at second end 178 to a linear slide 154b via a connecting link 130b. Linear slide 154a is mounted on non-rotating plate 156a and linear slide 154b is mounted on non-rotating plate 156b. The presence of the second non-rotating plate 156b, linear slide 154b and connecting link 130b is optional but contributes to providing a rigid frame upon which the connecting links and associated blades may slide without misalignment relative to the reference circle.

FIGS. 8a and 8b illustrate the use of the inventive apparatus in various stages of the size reduction process. In FIG. 8a, stent 180 has been placed in tubular aperture 162 which is characterized by a diameter $d_1$. In FIG. 8b, the device has been actuated by rotating actuation plate 142 so as to move blades 106 inward. Aperture 162, as shown in FIG. 8b is characterized by a diameter $d_2$ which is reduced relative to diameter $d_1$. Stent 180 is seen to be of reduced diameter relative to its previous diameter as shown in FIG. 8a.

Figure 8C:
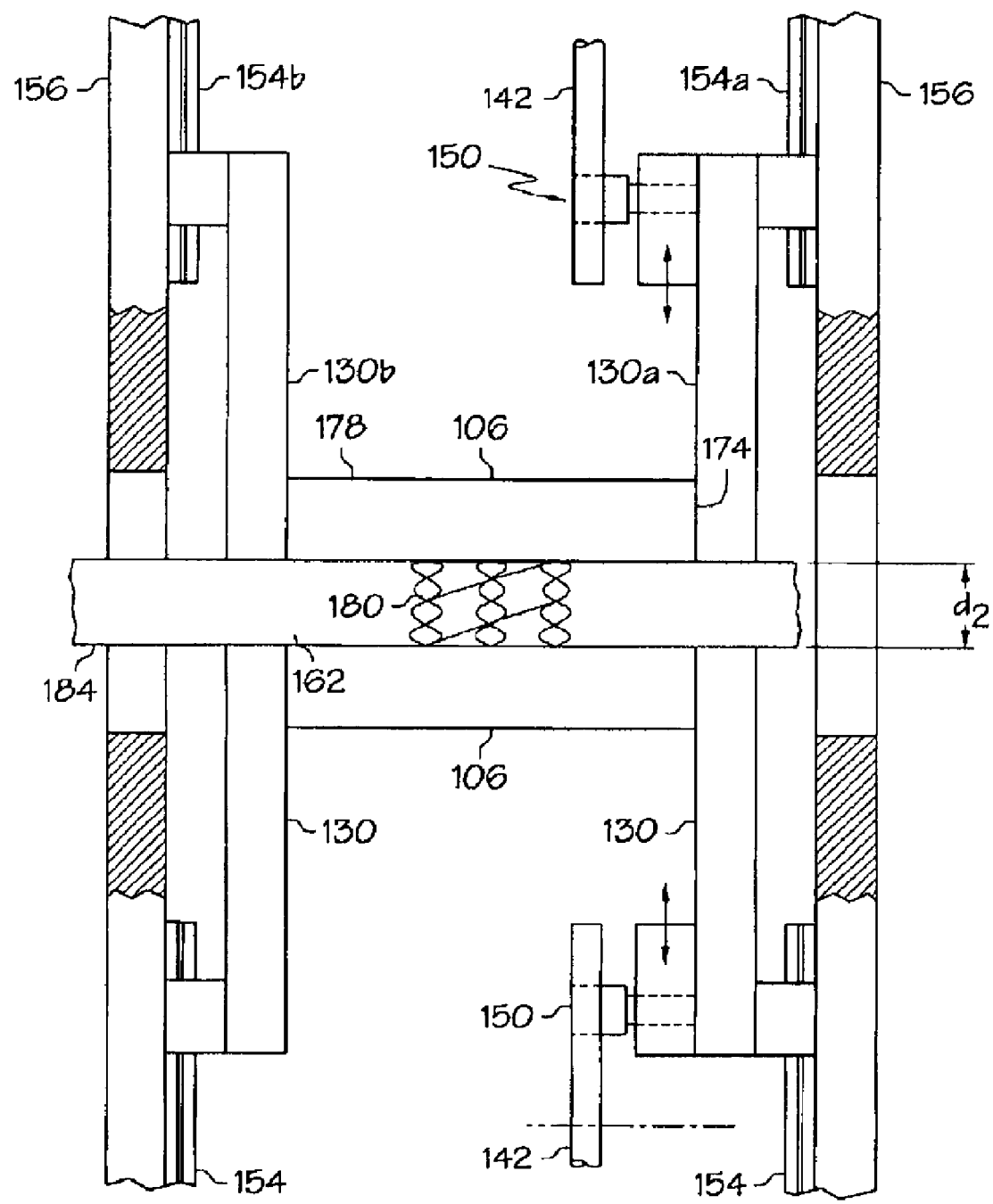
FIG. 8c is a partial side elevational view of an embodiment of the inventive apparatus taken along a radial plane following crimping of a stent to a catheter.

FIG. 8c differs from FIG. 8b, only in that stent 180 has been crimped onto catheter 184 in FIG. 8c.

Blades 106 may be made of any suitable, hard material including hardened steel. Desirably, the blades will be made of a material such as zirconia ceramic. Blades made of zirconia ceramic may be used without lubrication. Furthermore, because of their low thermal conductivity, they may be used to create a highly insulated chamber suitable for cryogenic processing of martensite in nitinol stents.

Figure 9:
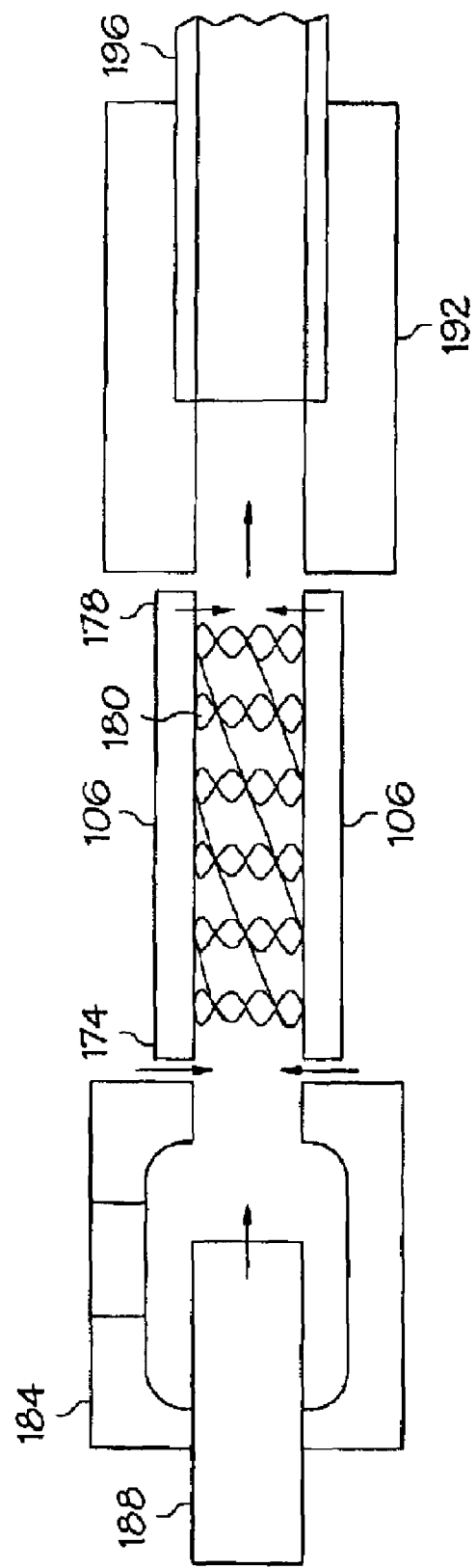
FIG. 9 is a diagrammatic side elevational view of an embodiment of the inventive apparatus.

Such an embodiment is shown in FIG. 9. Stent 180 is disposed between blades 106 which can move inward in the direction of the arrows. Blades 106 are cooled by a first source of cooling fluid 184 located at first end 174 of blades 106. Although not shown, a second source of cooling fluid may be provided at second end 178 of blades 106 as well. The cooling fluid may be a liquid cryogenic. Exemplary cryogenics include liquid nitrogen, argon or carbon dioxide although other cryogens may also be used. The cooling fluid may also be a chilled gas such as air. The cooling fluid may also be a cooled inert gas such as nitrogen, argon or other inert gasses.

The aperture formed by the blades is a highly insulated chamber which is suitable for cryogenic processing of martensite in nitinol stents. The chamber is maintained at −80° C. and a nitinol stent inserted therein. Upon equilibration of the temperature of the stent, the blades are moved inward to reduce the diameter of the stent. The stent is thus reduced in diameter while being maintained in the martensitic state.

The embodiment of FIG. 9 further has a loading plunger 188 for loading a stent or other suitable medical device into the aperture. A sheath housing 192 which houses sheath 196 is provided at second end 178 of blades 106. Plunger 188 may be further used to transfer the stent after it has been reduced in diameter or size to sheath 196. Desirably, sheath 196 will have a slightly larger diameter than stent 180 following reduction in size of the stent. More desirably, the fit of the stent within the sheath will be within about 1/32" and even more desirably, within about 1/64".

Where lengthy stents or other medical devices are to be reduced in size, the invention contemplates using one of the above described apparatuses with long blades to accommodate the stent. As an alternative, the invention also contemplates disposing two or more of such apparatuses sequentially to form one long aperture. The two or more apertures may then be reduced in size simultaneously or consecutively.

Figure 10:
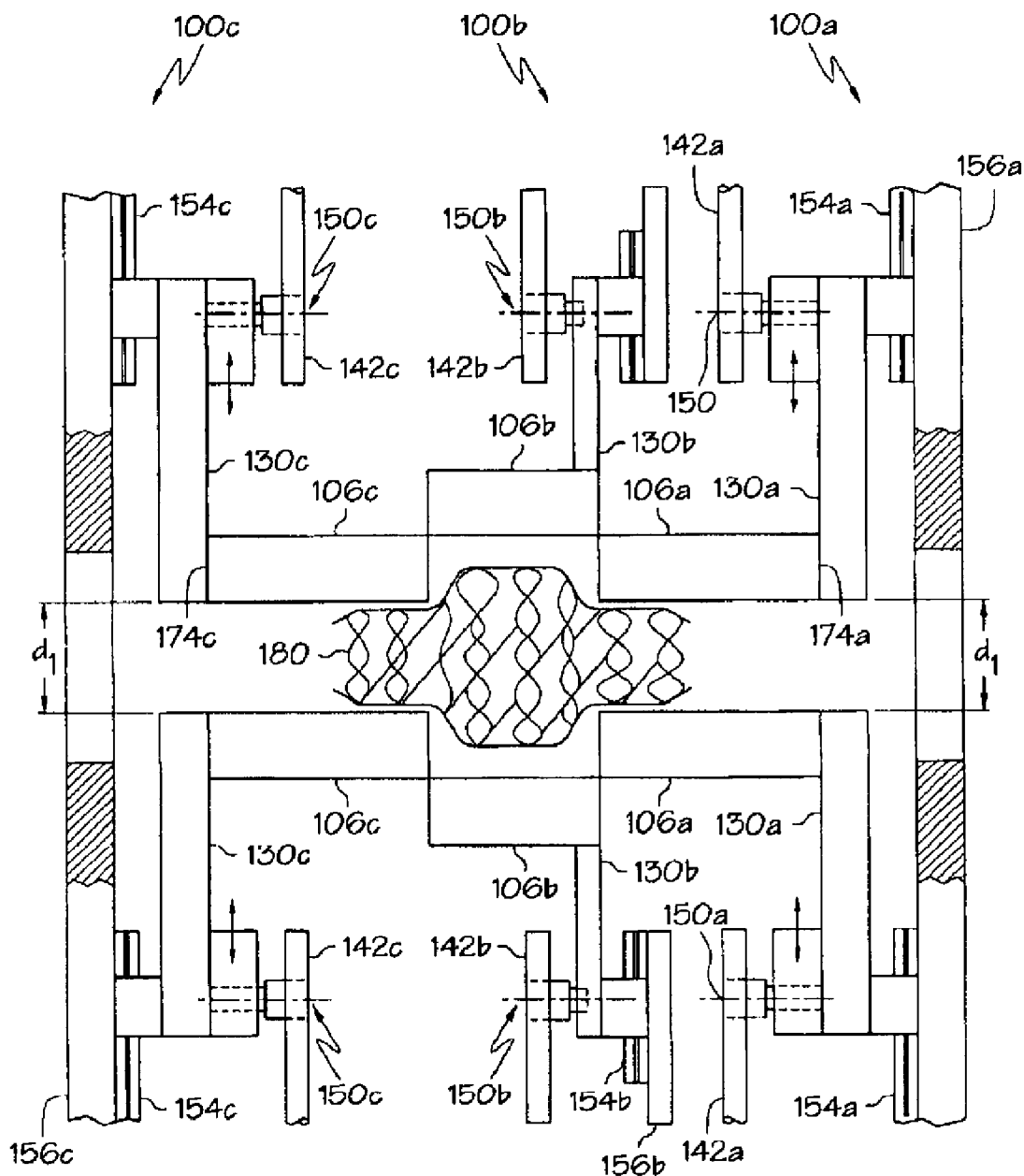
FIG. 10 is a partial side elevational view of an embodiment of the inventive apparatus taken along a radial plane of an embodiment of the invention consisting of three individual apparatuses arranged sequentially.

The arrangement of FIG. 10 shows an embodiment with three devices 100a-c arranged sequentially. A stepped reduction in size may be achieved by placing a stent 180 or similar medical device in the apparatus and independently reducing each aperture 118a-c to a desired size. To that end, the invention may provide particular utility in manipulating bifurcated stents or other stents whose diameter varies along its length. The embodiment of FIG. 10 shows the end portions of the stent being reduced in size prior to the middle portion of the stent. The device may also be operated so as to reduce the middle portion in size prior to the end portions or in any other sequence.

Figure 11:
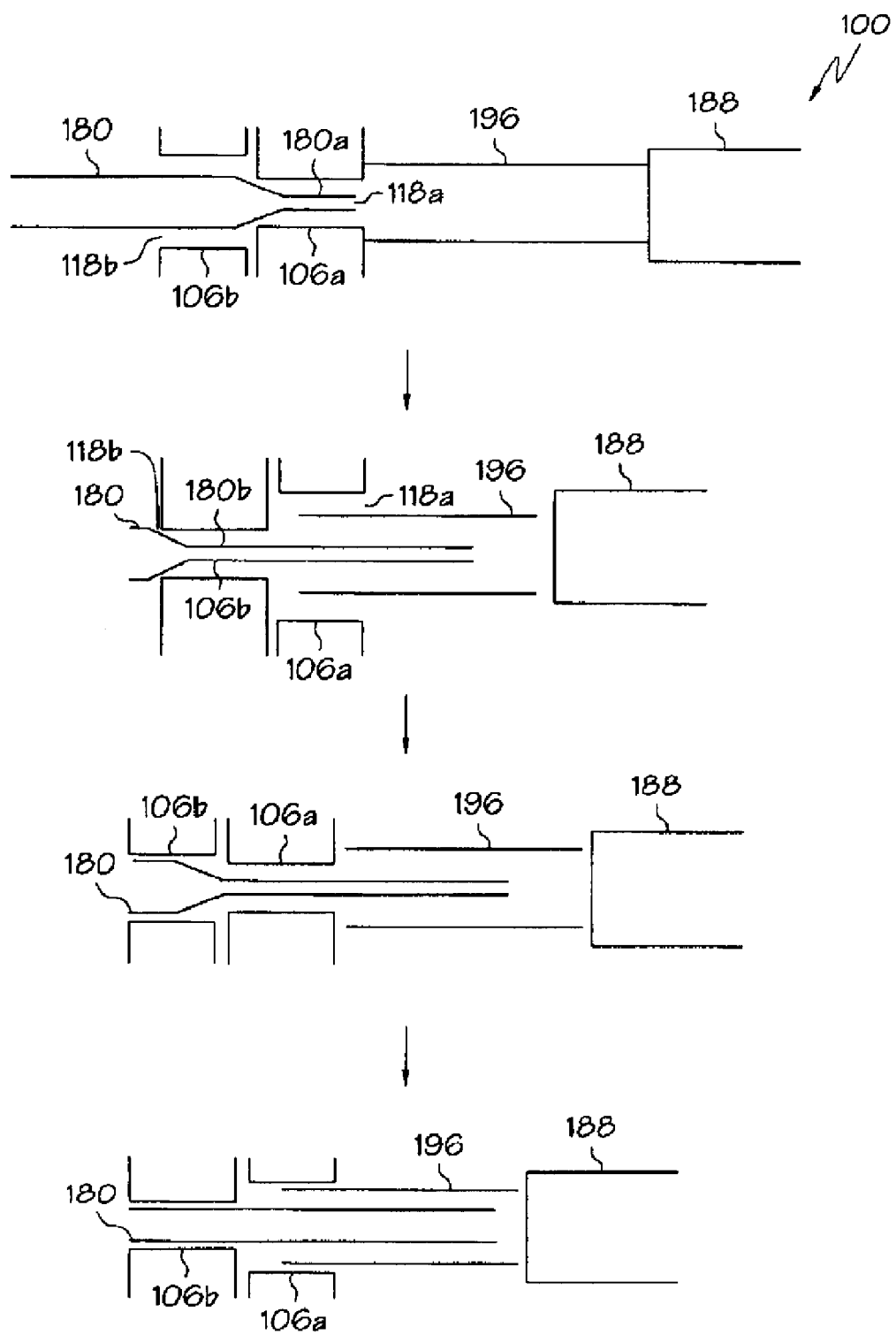
FIG. 11 is a schematic showing a stent being reduced in size and loaded into a sheath.

The invention contemplates yet another approach to reducing the diameter of lengthy stents or similar medical devices, namely walking the stent through the apparatus. This may be accomplished by either moving the stent relative to the apparatus or moving the apparatus relative to the stent as shown schematically in FIG. 11. To that end, stent 180 is inserted in device 100. Aperture 118a is reduced in size with blades 106a in turn reducing portion 180a of stent 180 in size. Aperture 118a is then opened and aperture 118b reduced in size thereby reducing portion 180b of stent 180. Simultaneously, or shortly thereafter, sheath 196 is pushed by plunger 188 over the portion of the stent that has been reduced in size. Aperture 118b is opened and the stent advanced in the apparatus. The process is repeated until the entire length, or the desired portion of the stent or medical device is reduced in size.

The reduction in size of the stent or other medical device may occur as part of a precrimping step or it may occur as part of crimping a stent onto a catheter and desirably, onto a balloon disposed about a catheter. In a general sense, it may be used for manipulating a medical device and specifically, for applying a radial inward force to a medical device.

In another embodiment, the invention is directed to a method of manipulating a medical device. As part of the method, a medical device such as those disclosed above is provided. The device has at least three blades capable of applying a radial inward force. The blades are disposed about a reference circle to form a shrinkable aperture. The blades are constructed and arranged such that each blade has only a single point which a) lies on the circumference of the reference circle prior to movement of the blade, and b) is moved along a radius of the reference circle on movement of the blade. The medical device is placed into the shrinkable aperture and the blades simultaneously moved inward to apply a radial inward force to the medical device and thereby reduce the medical device in size, and desirably, in diameter. Following reduction in size of the medical device, the blades are simultaneously moved outward and the medical device removed from the aperture.

Figure 12:
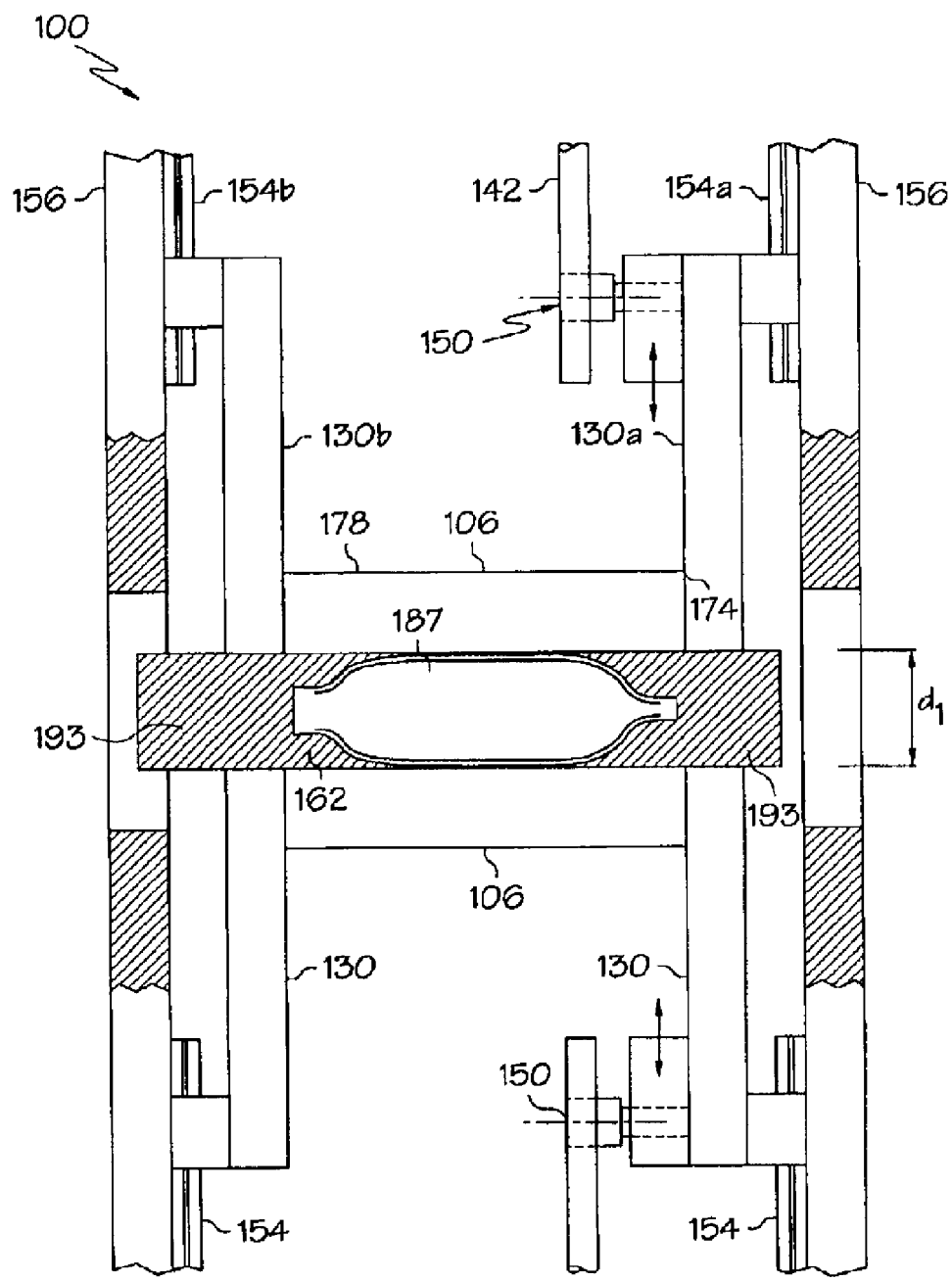
FIG. 12 is a partial side elevational view of an embodiment of the inventive apparatus taken along a radial plane showing a balloon that has been molded with the inventive device.

The inventive apparatus may also be incorporated into a blow molding tool to provide a variable size balloon mold as shown generally at 100 in FIG. 12. The various parts of the apparatus of FIG. 12 have been discussed in conjunction with FIGS. 8a-c and, with exception of balloon 181 and mold cavity ends 193, the reference numerals used in FIG. 12 correspond to those used for FIGS. 8a-c. Mold cavity ends 193 maybe provided in a variety of sizes and lengths to contain the balloon at each end. Desirably, the end molds will be adjustably mounted to a portion of the apparatus such as fixed plates 156 to provide for an adjustable length balloon mold.

The invention is also directed to a method for molding a medical balloon using the inventive apparatus described above. A balloon preform prepared through any standard method is provided. The inventive mold, shown generally at 100 is also provided. Balloon 181 is inserted into aperture 162. Aperture 162 is optionally reduced to a predetermined size and the preform expanded using standard techniques. An inflation fluid, for example, may be supplied to the preform and the preform expanded and heated. The balloon in its expanded state is shown in FIG. 12.

More generally, the invention may be practiced by providing at least three movable blades disposed about a reference tube to form a shrinkable tubular aperture. The blades are constructed and arranged such that each blade has a single line which a) lies on the surface of the reference tube prior to movement of the blade, and b) is moved along a radial plane of the reference tube on movement of the blade. A balloon preform is placed into the shrinkable aperture. The aperture may be set at a predetermined size prior to or following insertion of the balloon therein. An inflation fluid is provided and the balloon preform inflated so that the preform expands to the size of the aperture. The preform may be heated during this inflation/blowing step. The inflation fluid is then removed from the thus formed balloon and the balloon removed from the apparatus.

The balloon may also be molded in accordance with the method described in U.S. Pat. No. 5,163,989, or in accordance with other methods as are known to those of ordinary skill in the art, substituting the instant apparatus for the standard balloon mold. Other patents which discuss balloon molding include U.S. Pat. No. 5,807,520. Other references illustrating the materials and methods of making catheter balloons include: U.S. Pat. No. 4,413,989 and U.S. Pat. No. 4,456,000 to Schjeldahl et al, U.S. Pat. No. 4,490,421, U.S. Re 32,983 and Re 33,561 to Levy, and U.S. Pat. No. 4,906,244, U.S. Pat. No. 5,108,415 and U.S. Pat. No. 5,156,612 to Pinchuck et al.

The use of the inventive apparatus as a mold allows for the blowing of a balloon to a predetermined size using a single adjustable size balloon mold thereby eliminating the need to have multiple molds of different sizes.

Figure 13:
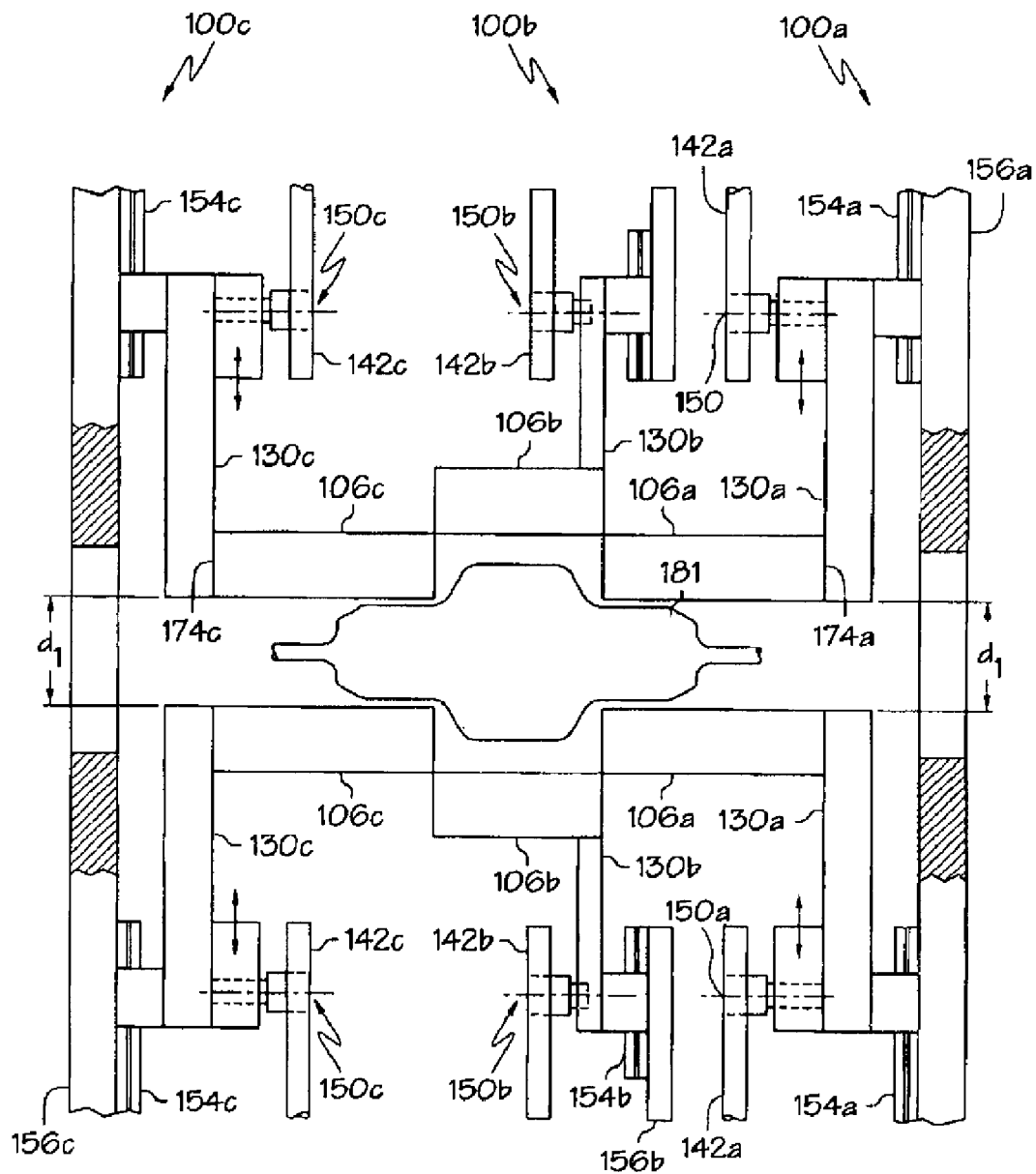
FIG. 13 is a partial side elevational view taken along a radial plane 5 showing a stepped balloon that has been molded with the inventive device.

The invention further contemplates molding a balloon to a desired shape using a plurality of the inventive devices arranged sequentially. As an example of this, shown in FIG. 13, a stepped balloon 181 maybe prepared by arranging several devices 100a, 100b and 100c sequentially. A balloon preform is inserted in the aperture formed by the device. The aperture of each device may be preset at a desired size or may be reduced in size to a predetermined size after the balloon preform is inserted therein. The balloon may then be blow molded in accordance with any suitable blow molding technique known in the art.

The invention is also understood to be directed to embodiments employing various combinations of the features disclosed herein.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A crimping apparatus for reducing the size of a stent, the crimping apparatus comprising:
a plurality of crimping devices arranged sequentially, each crimping device including a plurality of movable blades collectively arranged to form an iris defining an aperture of the crimping apparatus having a size which may be varied;
the plurality of movable blades of a first crimping device defining a first region of the aperture having a diameter and the plurality of movable blades of a second crimping device defining a second region of the aperture having a diameter different from the diameter of the first region; and
an actuator configured to actuate the plurality of movable blades to vary the size of the aperture.

2. The crimping apparatus of claim 1, wherein the aperture includes a third region defined by a plurality of movable blades of a third crimping device having a diameter different from the diameter of the second region.

3. The crimping apparatus of claim 2, wherein the diameters of the first and third regions are the same.

4. The crimping apparatus of claim 2, wherein the second region is positioned between the first region and the third region.

5. The crimping apparatus of claim 4, wherein the diameter of the second region is greater than the diameters of the first and third regions.

6. The crimping apparatus of claim 4, wherein the diameter of the second region is less than the diameters of the first and third regions.

7. The crimping apparatus of claim 4, wherein the first and third regions of the aperture are configured to reduce first and second end portions of a stent to a diameter less than a diameter of a central portion of the stent.

8. The crimping apparatus of claim 1, wherein the diameter of the first region of the aperture is varied independent of the diameter of the second region of the aperture.

9. The crimping apparatus of claim 2, wherein the diameter of the second region is varied independent of the diameters of the first and third regions of the aperture.

10. The crimping apparatus of claim 2, wherein the diameter of the second region is varied simultaneously with the diameters of the first and third regions of the aperture.

11. A system for crimping a stent onto a balloon of a balloon catheter, the system comprising:
a plurality of crimping devices including a first crimping device, a second crimping device and a third crimping device arranged sequentially, each crimping device including a plurality of movable blades collectively arranged to form an iris defining an aperture of the crimping apparatus having a size which may be varied by actuating the plurality of movable blades;
the first crimping device including a first subset of the plurality of movable blades defining a first region of the aperture having a diameter, the second crimping device including a second subset of the plurality of movable blades defining a second region of the aperture having a diameter, and the third crimping device including a third subset of the plurality of movable blades defining a third region of the aperture having a diameter greater than the diameters of the first and second regions, the third region positioned between the first region and the second region; and an actuator configured to actuate the plurality of movable blades to vary the size of the aperture.

12. The system of claim 11, wherein the first and third regions of the aperture are configured to reduce first and second end portions of a stent to a diameter less than a diameter of a central portion of the stent.

13. The system of claim 11, wherein the diameter of the second region is varied independent of the diameters of the first and third regions of the aperture.

14. The system of claim 13, wherein the second subset of movable blades is actuatable independent of the first and third subsets of movable blades.

15. The system of claim 11, wherein the diameter of the second region is varied simultaneously with the diameters of the first and third regions of the aperture.

16. The system of claim 15, wherein the second subset of movable blades is actuatable independent of the first and third subsets of movable blades.

* * * * *